United States Patent [19]

Reinholz et al.

[11] Patent Number: 4,906,666
[45] Date of Patent: Mar. 6, 1990

[54] HYDROXAMIC ACIDS AND PHARMACEUTICAL COMPOSITIONS CONTAINING THEM, AND ANTI-ALLERGIC USE THEREOF

[75] Inventors: Erhard Reinholz; Walter-Gunar Friebe, both of Mannheim; Wolfgang Kampe, Heddesheim, all of Fed. Rep. of Germany; Jürgen Mertin, Walenstadt, Switzerland; Otto-Henning Wilhelms, Mannheim, Fed. Rep. of Germany

[73] Assignee: Boehringer Mannheim GmbH, Mannheim, Fed. Rep. of Germany

[21] Appl. No.: 11,096

[22] Filed: Feb. 5, 1987

[30] Foreign Application Priority Data

Feb. 8, 1986 [DE] Fed. Rep. of Germany ....... 3604050

[51] Int. Cl.$^4$ ..................... A61K 31/045; C07C 83/10
[52] U.S. Cl. ..................................... 514/575; 514/541; 548/251; 548/252; 560/9; 560/12; 562/621
[58] Field of Search ................. 260/500.5 H; 514/507, 514/575

[56] References Cited

U.S. PATENT DOCUMENTS

| | | |
|---|---|---|
| 3,536,661 | 10/1970 | Hagemeyer, Jr. et al. . |
| 3,621,051 | 11/1971 | Heckenbleikner et al. . |
| 3,966,965 | 6/1976 | Sellstedt et al. ............. 260/500.5 H |
| 4,061,668 | 12/1977 | Orzalesi et al. ............. 260/500.5 H |
| 4,064,132 | 12/1977 | Janssen et al. ................ 260/500.5 H |
| 4,066,686 | 1/1978 | Lafon ........................... 260/500.5 H |
| 4,094,993 | 6/1978 | Karrer et al. . |
| 4,109,013 | 8/1978 | Grill et al. .................... 260/500.5 H |
| 4,497,827 | 2/1985 | Nelson ........................ 260/500.5 H |
| 4,534,911 | 8/1985 | Franz et al. ................. 260/500.5 H |
| 4,621,098 | 11/1986 | Umminger et al. . |
| 4,623,661 | 11/1986 | Summers ..................... 260/500.5 H |
| 4,661,505 | 4/1987 | Marshall et al. . |
| 4,728,670 | 1/1988 | Haslanger et al. .......... 260/500.5 H |

FOREIGN PATENT DOCUMENTS

| | | |
|---|---|---|
| 01018592 | 5/1984 | European Pat. Off. . |
| 0131221 | 1/1985 | European Pat. Off. . |
| 2008121 | 2/1969 | Fed. Rep. of Germany . |
| 2322137 | 8/1976 | France . |

OTHER PUBLICATIONS

Chemical Abstracts, Band 100, Nr. 25, Jun. 18, 1984, p. 556. Ref. Nr. 209381c, Columbus, Ohio, U.S.; & JP-A-58 222 064 (Taiho Pharmaceutical Co., Ltd.), 12/23/83.

Primary Examiner—David B. Springer
Attorney, Agent, or Firm—Felfe & Lynch

[57] ABSTRACT

The present invention provides compounds of the general formula:

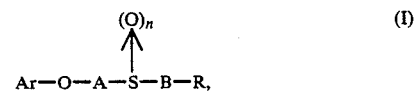

wherein Ar is a phenyl radical optionally substituted by alkyl, alkenyl, alkoxy, alkylthio, alkanoyl, hydroxyl, hydroxyalkyl, carboxyl, alkoxycarbonyl, carbamoyl, nitro, amino or halogen, A is a straight-chained or branched, saturated or unsaturated $C_1$–$C_8$ aliphatic hydrocarbon radical which is optionally substituted by a hydroxyl group, n is 0, 1 or 2, B is a straight-chained or branched, saturated or unsaturated $C_1$–$C_8$-aliphatic hydrocarbon radical and R is 5-(1H)-tetrazolyl, —CO—NH-tetrazolyl,

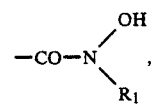

CN, SCN, OH, halogen, 5-(1H)-tetrazolylthio,

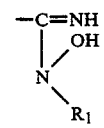

or CO—O—NH—$R_1$, wherein $R_1$ is a hydrogen atom, an alkyl radical optionally substituted by cycloalkyl or an alkenyl, cycloalkyl, aralkyl or aryl radical, wherein the aromatic moiety can be substituted by alkyl, alkenyl, alkoxy, alkylthio, alkanoyl, hydroxyl, hydroxyalkyl, carboxyl, alkoxycarbonyl, carbamoyl, nitro, amino or halogen; and the pharmacologically acceptable salts thereof. The present invention also provides processes for preparing these compounds and pharmaceutical compositions containing them for combating allergic diseases.

15 Claims, No Drawings

HYDROXAMIC ACIDS AND PHARMACEUTICAL COMPOSITIONS CONTAINING THEM, AND ANTI-ALLERGIC USE THEREOF

The present invention is concerned with new thioethers, processes for the preparation thereof and pharmaceutical compositions containing these compounds.

Analogous compounds are known from Federal Republic of Germany Patent Specification No. 33 24 916 and from European Patent Specification No. 0,131,221. However, in contradistinction to these known compounds, the new compounds according to the present invention have a stronger degree of action in the same dosage range.

In the case of oral and parenteral administration, the compounds according to the present invention inhibit anaphylactic and anaphylactoid reactions such as can be initiated, for example, on sensitised guinea pigs by allergen provocation. Moreover, they have an anti-inflammatory effect. Therefore, they are useful for combating allergic diseases, for example allergic asthma.

The new thioethers according to the present invention are compounds of the general formula:

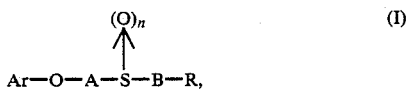

wherein Ar is a phenyl radical optionally substituted by alkyl, alkenyl, alkoxy, alkylthio, alkanoyl, hydroxyl, hydroxyalkyl, carboxyl, alkoxycarbonyl, carbamoyl, nitro, amino or halogen, A is a straight-chained or branched, saturated or unsaturated $C_1$-$C_8$ aliphatic hydrocarbon radical which is optionally substituted by a hydroxyl group, n is 0, 1 or 2, B is a straight-chained or branched, saturated or unsaturated $C_1$-$C_8$ aliphatic hydrocarbon radical and R is 5-(1H)-tetrazolyl, —CO—NH-tetrazolyl,

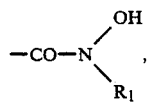

CN, SCN, OH, halogen, 5-(1H)-tetrazolylthio,

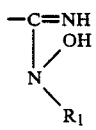

or —CO—O—NH—$R_1$, wherein $R_1$ is a hydrogen atom, an alkyl radical optionally substituted by cycloalkyl or an alkenyl, cycloalkyl, aralkyl or aryl radical, wherein the aromatic moiety can be substituted by alkyl, alkenyl, alkoxy, alkylthio, alkanoyl, hydroxyl, hydroxyalkyl, carboxyl, alkoxycarbonyl, carbamoyl, nitro, amino or halogen; as well as the pharmacologically acceptable salts thereof.

The above-mentioned alkyl radicals as such or as parts of other radicals contain up to 6 carbon atoms and can be straight-chained or branched.

In particular, alkyl can be a methyl, ethyl, propyl or butyl radical, alkoxy can be a methoxy or ethoxy radical, alkylthio can be an methylthio radical, hydroxyalkyl can be a hydroxymethyl, hydroxyethyl, hydoxypropyl, hydroxybutyl, hydroxypentyl or hydroxyhexyl radical, the hydroxyl substituent being at any desired position of the alkyl chain, and alkoxycarbonyl can be a methoxycarbonyl or ethoxycarbonyl radical.

Alkanoyl radicals preferably contain up to 4 carbon atoms, for example formyl, acetyl or propionyl.

Cycloalkyl radicals preferably contain 3 to 7 carbon atoms, especially cyclopentyl and cylcohexyl.

The aralkyl radical is preferably a benzyl or phenethyl radical.

The group A represents a $C_1$-$C_8$ aliphatic hydrocarbon radical, those with 2 to 5 carbon atoms being preferred, for example ethylene, propylene and butylene, in which case the propylene radical in particular can contain a hydroxyl substituent. Unsaturated radicals are preferably —$CH_2$—CH=CH—$CH_2$— or —$CH_2$—C≡C—$CH_2$—.

The group B is a $C_1$-$C_8$ aliphatic hydrocarbon radical, preferably methylene, ethylene, propylene, butylene or pentylene. A branched alkylene radical is preferably the —C($CH_3$)$_2$—$CH_2$— radical. Unsaturated radicals are, in particular, —$CH_2$—CH=CH— and —$CH_2$—C≡C—.

The alkenyl radical contains 2 to 6 carbon atoms, the allyl radical being preferred.

The halogen atoms are fluorine, chlorine or bromine.

Preferred compounds are those in which Ar is substituted one, two or three times, Ar being a methoxyphenyl, pentylphenyl, hydroxyhexylphenyl, dichlorophenyl, 4-acetyl-3-hydroxy-2-propylphenyl or 4-acetyl-2-allyl-3-hydroxyphenyl radical or R is N-hydroxy-N-methylaminocarbonyl, N-ethyl-N-hydroxyaminocarbonyl, N-cyclohexyl-N-hydroxyaminocarbonyl, 5-tetrazolylaminocarbonyl, 5-tetrazolyl, 5-tetrazolylthio, N-hydroxyaminocarbonyl, hydroxyl, halo, cyano or thiocyanato.

Apart from the compounds mentioned hereinafter in the specific Examples, the present invention also includes all compounds which display every possible combination of the substituents mentioned in the Examples.

The present invention also provides pharmaceutical compositions containing at least one compound of general formula (I) and is also concerned with the use of such compounds of general formula (I) for the preparation of such compositions.

The present invention also provides a process for the preparation of compounds of general formula (I), wherein either (a) a compound of the general formula:

is reacted with a compound of the general formula:

in which Ar, A and B have the same meanings as above, one of the symbols X and Y represents an —SH group and the other a relative residue and G has the same meaning as R above or is a hydroxyl group; or (b) a compound of the general formula:

in which Ar, A and B have the same meanings as above, or a reactive derivative thereof, for example a carboxylic acid halide, carboxylic acid ester or a mixed carboxylic acid anhydride, is reacted with 5-amino-(1H)-tetrazole or with a compound of the general formula:

HO—NH—R₁     (V), in which R₁ has the same meaning as above, or with an O-silylated derivative thereof; whereafter, if desired, when G is a hydroxyl group, this is first converted, for example, into a reactive derivative, such as a halide, mesylate or tosylate, and then converted into a radical R, a radical R is optionally converted into a different radical R, the sulphur atom is optionally oxidised and the reaction product obtained is, if desired, converted into a pharmacologically acceptable salt.

Examples of reactive residues X and Y in compounds (II) and (III) include chlorine, bromine, mesyloxy and tosyloxy. Compounds of the general formulae (II) and (III), in which Y is an —SH group, can be used as such or can be liberated in situ from an appropriate precursor, for example an S-alkylated 3-thio-1,2-benzisothiazole-1,1-dioxide or an S-alkylated isothiuronium salt.

Conversion of a radical R into a different radical R as defined hereinbefore can take place, for example, by reacting a compound of general formula (I), in which R is a cyano or thiocyanato group, with hydrazoic acid or with an alkali metal azide and a proton-providing substance, for example ammonium chloride or with a compound of general formula (V).

The starting materials of general formulae (III) and (V) are either known from the literature or can be prepared analogously to processes known from the literature.

The preparation of compounds of general formulae (II) and (IV) is known from European Patent Specification No. 0,131,221.

The process according to the present invention is carried out, for example, by first reacting a compound of general formula (II), in which X is a reactive residue, with a derivative of 3-thio-1,2-benzisothiazole-1,1-dioxide which carries a —B—G radical on the sulphur atom, in the presence of an equimolar amount of a secondary amine, the reaction product obtained then being isolated.

The reaction is preferably carried out in a polar, aprotic solvent, for example acetonitrile, in the presence of a tertiary amine.

If desired, the reaction product obtained can be reacted in a polar, aprotic solvent with an alkali metal azide or ammonium azide.

According to another variant of the process, a compound of general formula (II) in which X is an —SH group, is alkylated with a compound of general formula (III), in which Y is a reactive residue.

When G is a hydroxyl group, the product obtained by reaction with a compound of general formula (II) can be converted, for example, by reaction with triphenylphosphine and a tetrahalomethane in a halogenated hydrocarbon, into a halide from which, by reaction in a polar, aprotic solvent, for example acetone, with an alkali metal cyanide or alkali metal thiocyanate there is obtained a compound of general formula (I).

An oxidation of the sulphur atom in compounds of general formula (I) can be carried out, for example, by oxidising according to known methods, for example with oxygen, hydrogen peroxide, tert.-butyl hydroperoxide or an organic per acid, in a solvent, such as dichloromethane, acetone or acetic acid, to give the corresponding sulphoxide or sulphone.

Especially preferred pharmacologically acceptable salts include the alkali metal, alkaline earth metal and ammonium salts, as well as possibly salts with nontoxic inorganic and organic acids, for example, hydrochloric acid, sulphuric acid, phosphoric acid, hydrobromic acid, acetic acid, lactic acid, citric acid, malic acid, benzoic acid, salicylic acid, malonic acid, maleic acid, succinic acid or diaminocaproic acid.

The salts are obtained in the usual manner, for example by neutralising a compound of general formula (I) with an appropriate base or acid.

For the preparation of pharmaceutical compositions, the compounds of general formula (I) are mixed in known manner with appropriate pharmaceutical carrier substances, aroma, flavouring and colouring materials, and formed, for example, into tablets or dragees or, with the addition of appropriate adjuvants, suspended or dissolved in water or in an oil, for example olive oil.

The compounds of general formula (I) can be administered orally and parenterally in liquid or solid form. As injection medium, it is preferred to use water which contains the stabilising agents, solubilising agents and/or buffers usual in the case of injection solutions. Such additives include, for example, tartrate and borate buffers, ethanol, dimethyl sulphoxide, complex formers (such as ethylenediaminetetraacetic acid), high molecular weight polymers (such as liquid polyethylene oxide) for viscosity regulation or polyethylene derivatives of sorbitan anhydrides.

Solid carrier materials include, for example, starch, lactose, mannitol, methyl cellulose, talc, highly dispersed silicic acid and high molecular weight polymers (such as polyethylene glycols).

Compositions suitable for oral administration can, if desired, contain flavouring and sweetening agents. For external application, the compounds of general formula (I) according to the present invention can be used in the form of powders or salves. For this purpose, they are mixed, for example, with powdered, physiologically compatible dilution agents or conventional salve bases.

The dosage administered depends upon the age, the state of health and the weight of the recipient, the extent of the disease, the nature of further treatments carried out simultaneously, the frequency of the treatment and the nature of the desired action. The daily dosage of the active compound is usually from 0.1 to 50 mg./kg. body weight. Normally, 0.5 to 40 and preferably 1.0 to 20 mg./kg./day in one or more administrations per day are effective in order to obtain the desired results.

Apart from the compounds mentioned hereinafter in the specific Examples, preferred compounds according to the present invention also include the following:
N-hydroxy-N-prop-2-enyl-S-[3-(4-acetyl-3-hydroxy-2-propyl-phenoxy)-propyl]-3-thiopropionic acid amide,
5-[S-(4-{4-acetyl-3-hydroxy-2-propylphenoxy}-butyl)-2-thioethyl]-(1H)-tetrazole;
N-hydroxy-S-[4-(4-acetyl-3-hydroxy-2-propylphenoxy)butyl]-3-thiopropionic acid amidine.

The following Examples are given for the purpose of illustrating the present invention:

EXAMPLE 1

N-Hydroxy-N-methyl-S-[3-(4-acetyl-3-hydroxy-2-propylphenoxy)-propyl]-thioacetamide 2.6 g (8 mMole) S-[3-(4-acetyl-3-hydroxy-2-propylphenoxy)-propyl]-thioacetic acid are dissolved in 30 ml. methylene chloride, mixed with 0.81 g. (8 mMole) 4-methylmorpholine and cooled to $-10°$ to $-15°$ C. 1.15 g. (8 mMole) isobutyl chloroformate in 10 ml. methylene chloride is added dropwise at this temperature within the course of 10 minutes. Subsequently, the reaction mixture is further stirred for 15 minutes at the same temperature and then mixed with 0.47 g. N-methylhydroxylamine in 10 ml. methylene chloride.

The reaction mixture is then stirred for 1 hour at $-10°$ C. and for 2 hours at 0° C. and subsequently warmed up to ambient temperature. The methylene chloride is then stripped off and the residue boiled up twice with ligroin. The residue thus obtained is dissolved in ethyl acetate and extracted three times with 2M aqueous sodium hydroxide solution. The aqueous phase is acidified and extracted three times with diethyl ether. For removing unreacted starting material, the ethereal solution is extracted three times with 2M aqueous sodium carbonate solution. The ethereal solution is subsequently washed with water, 2M hydrochloric acid and water, dried and evaporated. There is obtained 1.3 g. (46% of theory) of the title compound in the form of an oil.

EXAMPLE 2

The following compounds are obtained in a manner analogous to that described in Example 1:

| designation | | Yield % | m.p. (°C.) (solvent) |
|---|---|---|---|
| (a) | N—hydroxy-N—methyl-S—[3-(2-pentylphenoxy)-propyl]-3-thiopropionic acid amide | 60 | oil |
| (b) | N—hydroxy-N—methyl-S—[3-(3-pentylphenoxy)-propyl]-3-thiopropionic acid amide | 50 | oil |
| (c) | N—hydroxy-N—methyl-S—[4-(4-acetyl-3-hydroxy-2-propylphenoxy)-butyl]-3-thiopropionic acid amide | 71 | oil |
| (d) | N—hydroxy-N—methyl-S—[3-(4-acetyl-3-hydroxy-2-propylphenoxy)-propyl]-6-thiohexanoic acid amide | 42 | oil |
| (e) | N—hydroxy-N—methyl-S—[4-(4-acetyl-3-hydroxy-2-allyl-phenoxy)-but-2-ynyl)-3-thiopropionic acid amide | 30 | oil |
| (f) | N—hydroxy-N—methyl-S—[4-(4-acetyl-3-hydroxy-2-propyl-phenoxy)-butyl]-thioacetamide | 70 | oil |
| (g) | N—hydroxy-N—methyl-S—[4-(acetyl-3-hydroxy-2-propyl-phenoxy)-but-2-ynyl]-3-thiopropionic acid amide | 32 | oil |
| (h) | N—hydroxy-N—methyl-S—[3-(4-acetyl-3-hydroxy-2-allyl-phenoxy)-propyl]-3-thiopropionic acid amide | 35 | oil |
| (i) | N—hydroxy-N—methyl-S—[3-(4-acetyl-3-hydroxy-2-propyl-phenoxy)-propyl]-3-thiopropionic acid amide | 40 | 112–9 (ligroin/ diethyl ether) |
| (j) | N—hydroxy-N—methyl-S—(3-phenoxypropyl)-3-thiopropionic acid amide | 85 | oil |
| (k) | N—hydroxy-N—methyl-S—[3-(3-methoxyphenoxy)-propyl]-3-thiopropionic acid amide | 65 | oil |
| (l) | N—hydroxy-N—methyl-S—[3-(3-{1-hydroxyhexyl}-phenoxy)-propyl]-4-thiobutyric acid amide | 56 | oil |
| (m) | N—hydroxy-N—methyl-S—[3-(3-{1-hydroxyhexyl}-phenoxy)-2-hydroxypropyl]-4-thiobutyric acid amide | 65 | oil |
| (n) | N—hydroxy-N—methyl-S—[4-(3-{1-hydroxyhexyl}-phenoxy)-butyl]-3-thiopropronic acid amide | 52 | oil |
| (o) | N—hydroxy-N—methyl-S—[4-(3-{1-hydroxyhexyl}-phenoxy)-but-2-enyl]-3-thiopropionic acid amide | 15 | oil |
| (p) | N—hydroxy-N—methyl-S—[3-(4-acetyl-3-hydroxy-2-propyl-phenoxy)-2-hydroxypropyl]-3-thiopropionic acid amide | 47 | oil |
| (q) | N—hydroxy-N—ethyl-S—[3-(4-acetyl-3-hydroxy-2-propyl-phenoxy)-propyl]-3-thiopropionic acid amide | 68 | 56 (ligroin) |
| (r) | N—hydroxy-N—propyl-S—[3-(4-acetyl-3-hydroxy-2-propyl-phenoxy)-propyl]-3-thiopropionic acid amide | 77 | 57–60 (ligroin) |
| (s) | N—hydroxy-N—phenyl-S—[3-(4-acetyl-3-hydroxy-2-propyl-phenoxy)-propyl]-3-thiopropionic acid amide | 70 | 64–66 (ligroin) |
| (t) | O—[S—(3-{4-acetyl-3-hydroxy-2-propylphenoxy}-propyl)-3-thiopropionyl]-cyclohexyl-hydroxylamine | 14 | oil |
| (u) | N—hydroxy-N—methyl-S—[5-(4-acetyl-3-hydroxy-2-propyl-phenoxy)-pentyl]-3-thiopropionic acid amide | 31 | 76 (ligroin) |
| (v) | N—hydroxy-N—methyl-S—[3-(3,4-dichloro-2-propylphenoxy)-propyl]-3-thiopropionic acid amide | 42 | 35–36 (ligroin) |

EXAMPLE 3

N-[(1H)-Tetrazol-5-yl]-S-[3-(2-pentylphenoxy)-propyl]-3-thiopropionic acid amide 0.9 g. (29 mMole) S-[3-(2-pentylphenoxy)-propyl]-3-thiopropionic acid are dissolved in 10 ml. methylene chloride and mixed with 0.29 g. (29 mMole) N-methylmorpholine. The reaction mixture is cooled to $-10°$ C. and 0.39 g. (29 mMole) isobutyl chloroformate in 5 ml. methylene chloride added dropwise thereto at this temperature. The reaction mixture is further stirred for 15 minutes and thereafter a suspension of 0.3 g. (29 mMole) 5-amino-(1H)-tetrazole in 5 ml. methylene chloride is added thereto. Stirring is carried out for 1 hour at $-10°$ C. and for 1.5 hours at 0° C., whereafter the reaction mixture is allowed to warm up to ambient temperature. The methylene chloride is then evaporated off and the residue is mixed with ethyl acetate and extracted with 2M hydrochloric acid. The ethyl acetate phase is dried and evaporated.

After chromatography on silica gel using the system ligroin/ethyl acetate (1:2 v/v) with 0.25% acetic acid, there is obtained 0.4 g. (37% of theory) of the title compound; m.p. 151°–168° C.

EXAMPLE 4

The following compounds are obtained in a manner analogous to that described in Example 1:

| designation | | yield % | m.p. (°C.) (solvent) |
|---|---|---|---|
| (a) | N—[(1H)-tetrazol-5-yl]-S—[3-(4-acetyl-3-hydroxy-2-allyl-phenoxy)-propyl]-3-thio-propionic acid amide | 25 | 209 (methanol) |
| (b) | N—[(1H)-tetrazol-5-yl]-S—[3-(4-acetyl-3-hydroxy-2-propyl-phenoxy)-propyl]-6-thio-hexanoic acid amide | 40 | 190–3 (ethyl acetate) |
| (c) | N—[(1H)-tetrazol-5-yl]-S—[3-(3-{1-hydroxyhexyl}-phenoxy)-propyl]-4-thiobutyric acid amide | 40 | 175–82 (isopropanol) |
| (d) | N—[(1H)-tetrazol-5-yl]-S—[3-(3-{(1-hydroxyhexyl)-phenoxy)-2-hydroxypropyl]-4-thio-butyric acid amide | 50 | 164–7 (diethyl ether) |
| (e) | N—[(1H)-tetrazol-5-yl]-S—[4-(3-{1-hydroxyhexyl}-phenoxy)-butyl]-3-thiopropionic acid amide | 36 | 148–50 (water) |
| (f) | N—[(1H)-tetrazol-5-yl]-S—[4-(3-{1-hydroxyhexyl}-phenoxy)-but-2-enyl]-3-thiopropionic acid amide | 15 | 145–8 (dichloromethane/methanol |
| (g) | N—[(1H)-tetrazol-5-yl]-S—[3-(3,4-dichlorophenoxy)-propyl]-3-thiopropionic acid amide | 45 | 165–7 (diethyl ether) |
| (h) | N—[(1H)-tetrazol-5-yl]-S—[4-(4-acetyl-3-hydroxy-2-propyl-phenoxy)-but-2-ynyl]-3-thio-propionic acid amide | 43 | 178–81 (diethyl ether/acetone) |
| (i) | N—[(1H)-tetrazol-5-yl]-S—[3-(4-chlorophenoxy)-propyl]-3-thiopropionic acid amide | 55 | 160–62 (water) |
| (j) | N—[(1H)-tetrazol-5-yl]-S—[3-(4-chloro-3-trifluoromethyl-phenoxy)-propyl]-3-thio-propionic acid amide | 68 | 174–76 (isopropanol) |

EXAMPLE 5

5-{S-[3-(4-Acetyl-3-hydroxy-2-allylphenoxy)-propyl]-thiomethyl}-(1H)-tetrazole 2.1 g. (7 mMole) S-[3-(4-acetyl-3-hydroxy-2-allyl-phenoxy)-propyl]-thioacetonitrile are dissolved in 50 ml. dimethylformamide, mixed with 2.27 g. (35 mMole) sodium azide and 1.87 g. (35 mMole) ammonium chloride and stirred for 48 hours at 120° C. and 150 bar nitrogen.

The dimethylformamide is then evaporated off and the residue is mixed with sodium hydroxide and filtered. The solution is shaken out with methylene chloride, subsequently acidified and the product is extracted with methylene chloride.

After chromatographing on silica gel with the system methylene chloride/methanol/water (325:225:25 v/v/v), there is obtained 0.6 g. (25% of theory) of the title compound; m.p. 129°–132° C.

EXAMPLE 6

The following compounds are obtained in a manner analogous to that described in Example 5.

| designation | | yield % | m.p. (°C.) (solvent) |
|---|---|---|---|
| (a) | 5-{S—[3-(4-acetyl-3-hydroxy-2-propylphenoxy)-propyl]-5-thiopentyl}-(1H)-tetrazole | 28 | 93 (dichloromethane/methanol) |
| (b) | 5-{S—[3-(4-acetyl-3-hydroxy-2-propylphenoxy)-propyl]-2-thioethyl}-(1H)-tetrazole | 41 | 126 (dichloromethane/methanol) |
| (c) | 5-{S—[3-(2-pentylphenoxy)-propyl]-2-thioethyl}-(1H)-tetrazole | 36 | 51 (ligroin) |
| (d) | 5-{S—[3-(4-acetyl-3-hydroxy-2-allylphenoxy)-propyl]-2-thioethyl}-(1H)-tetrazole | 32 | 112–9 (water) |

EXAMPLE 7

{S-[3-(4-Acetyl-3-hydroxy-2-propylphenoxy)-propyl]-2-thioethyl}-5-mercapto-(1H)-tetrazole 0.7 g (2 mMole) S-[3-(4-acetyl-3-hydroxy-2-propyl-phenoxy)-propyl]-2-thioethyl thiocyanate is dissolved in 25 ml. dimethylformamide and mixed with 0.65 g. (10 mMole) sodium azide and 0.53 g. (10 mMole) ammonium chloride in a steel autoclave. The mixture is allowed to react for 24 hours at 95° C. and 150 bar nitrogen pressure. Subsequently, the dimethylformamide is distilled off and the residue is mixed with 2M aqueous sodium hydroxide solution and extracted with ethyl acetate. The aqueous phase is acidified with 2M hydrochloric acid and extracted with ethyl acetate. After evaporation, the residue is boiled with cyclohexane to give 0.22 g. (28% of theory) of the title compound; m.p. 96°–97° C.

EXAMPLE 8

N-Hydroxy-S-[3-(2-pentylphenoxy)-propyl]-3-thiopropionic acid amide 2.08 g. (15 mMole) Hydroxylamine hydrochloride are dissolved in 30 ml. methanol and mixed with 45 ml. 1M sodium methylate solution. After 30 minutes, 4.87 g. methyl (15 mMole) S-[3-(2-pentylphenoxy)-propyl]-3-thiopropionate in 30 ml. methanol are added dropwise thereto and the reaction mixture is subsequently boiled under reflux for 4 hours. Salt is removed by filtration and the filtrate is evaporated. The residue is then dissolved in ethyl acetate and the solution further worked up as in Example 1. There are obtained 2.0 g. (41% of theory) of the title compound in the form of an oil.

EXAMPLE 9

The following compounds are obtained in an manner analogous to that described in Example 8:

| designation | | yield % | m.p. (°C.) (solvent) |
|---|---|---|---|
| (a) | N—hydroxy-S—[3-(3-{1-hydroxyhexyl}-phenoxy)-propyl]-4-thiobutyric acid amide | 54 | oil |
| (b) | N—hydroxy-S—[3-(3-{1-hydroxyhexyl}-phenoxy)-2-hydroxypropyl]-4-thiobutyric acid amide | 36 | oil |
| (c) | N—hydroxy-S—[4-(3-{1-hydroxyhexyl}phenoxy)-butyl]-3-thiopropionic acid amide | 20 | oil |
| (d) | N—hydroxy-S—[4-(3-{1-hydroxyhexyl}-phenoxy)-but-2-enyl]-3-thiopropionic acid amide | 41 | oil |

-continued

| designation | | yield % | m.p. (°C.) (solvent) |
|---|---|---|---|
| (e) | N—hydroxy-S—[3-(3-pentyl-phenoxy)-propyl]-3-thio-propionic acid amide | 32 | oil |

EXAMPLE 10

S-[3-(4-Acetyl-3-hydroxy-2-propylphenoxy)-propyl]-2-mercaptoethanol 4.68 g. (60 mMole) 2-mercaptoethanol are stirred for 10 minutes at ambient temperature with 60 ml. 1M sodium methylate solution. Subsequently, 9.39 g. 3-(4-acetyl-3-hydroxy-2-propylphenoxy)-propyl bromide are added thereto and the reaction mixture is boiled under reflux for 5 hours. The reaction mixture is thereafter evaporated and the residue mixed with water and ethyl acetate. The ethyl acetate phase is successively shaken with 2M aqueous sodium hydroxide solution and with 2M hydrochloric acid and then dried and evaporated. After recrystallising the residue from diethyl ether/ligroin, there are obtained 6.4 g. (68% of theory) of the title compound; m.p. 72°–74° C.

EXAMPLE 11

S-[3-4-Acetyl-3-hydroxy-2-propylphenoxy)-propyl]-2-mercaptoethyl bromide 1.63 g. (5 mMole) S-[3-(4-acetyl-3-hydroxy-2-propyl-phenoxy)-propyl]-2-mercaptoethanol are dissolved in 15 ml. methylene chloride and mixed with 2.07 g. (6.25 mMole) tetrabromomethane. The mixture is cooled to −10° C. and mixed portionwise with 1.96 g. (7.5 mMole) triphenyl phosphine. After stirring for 15 minutes, the reaction mixture is mixed with diethyl ether and the precipitate obtained is filtered off with suction. The diethyl ether is evaporated off and the residue is mixed with hexane. After filtering off the precipitate and evaporating the hexane, there is obtained 1.7 g. (91% of theory) of the title compound; m.p. 74°–75° C.

EXAMPLE 12

S-[3-(4-Acetyl-3-hydroxy-2-propylphenoxy)-propyl]-2-mercaptoethyl thiocyanate 1.0 g. (2.8 mMole) S-[3-(4-acetyl-3-hydroxy-2-propyl-phenoxy)-propyl]-2-mercaptoethyl bromide and 5.0 g. potassium thiocyanate are heated to reflux for 2 hours in 25 ml. acetone. Subsequently, the precipitate is filtered off with suction, the solution is evaporated and the residue is stirred with diethyl ether. After evaporating the diethyl ether, there is obtained 0.7 g. (71% of theory) of the title compound in the form of an oil.

EXAMPLE 13

S-[3-(4-Acetyl-3-hydroxy-2-allylphenoxy)-propyl]-3-mercaptopropionitrile 1.6 g. (6.3 mMole) 3-(3-mercaptopropionitrile)ben-zoisothiazole-S,S-dioxide is suspended in 10 ml. acetonitrile under an atmosphere of nitrogen. 0.52 ml. piperidine is added thereto and the reaction mixture is stirred for 20 minutes at ambient temperature. Subsequently, 0.92 g. DBU and 1.87 g. (6 mMole) 3-(4-acetyl-3-hydroxy-2-allylphenoxy)-propyl bromide are added thereto and the reaction mixture is stirred for 30 minutes at ambient temperature. After evaporation, the residue is dissolved in ethyl acetate, shaken with 2M aqueous sodium hydroxide solution, washed neutral, dried and evaporated. After boiling with ligroin and evaporation, there is obtained 1.2 g. (63% of theory) of the title compound in the form of an oil.

EXAMPLE 14

The following compounds are obtained in a manner analogous to that described in Example 13:

| designation | | yield % | m.p (°C.) (solvent) |
|---|---|---|---|
| (a) | S—[3-(4-acetyl-3-hydroxy-2-propylphenoxy)-propyl]-6-thiohexane nitrile | 55 | oil |
| (b) | S—[3-(4-acetyl-3-hydroxy-2-allylphenoxy)-propyl]-thio-acetonitrile | 48 | 71 (ligroin) |
| (c) | S—[3-(4-acetyl-3-hydroxy-2-propylphenoxy)-propyl]-3-thiopropionitrile | 49 | 42 (dichloro-methane) |
| (d) | S—3-(2-pentylphenoxy)-propyl]-3-thiopropionitrile | 60 | oil |

EXAMPLE 15

Analogously to Example 2t but with the use of 0-trimethylsilyl-cyclohexylhydroxylamine there is obtained the following compound:

| designation | yield % | m.p. (°C.) (solvent) |
|---|---|---|
| N—hydroxy-N—cyclohexyl-S—[3-(4-acetyl-3-hydroxy-2-propyl-phenoxy)-propyl]-3-thio-propionic acid amide | 36 | 124–5-(ligroin/acetone) |

The intermediates are prepared as follows:

(a) [3-(1-Hydroxyhexyl)-phenoxymethyl]-oxirane 19.4 g. (0.1 mole) 3-(1-hydroxyhexyl)-phenol and 28.6 g. epichlorohydrin are dissolved in 25 ml. ethanol and heated to the boil. A solution of 6.6 g. potassium hydroxide in 3 ml. water and 25 ml. ethanol is then added dropwise thereto in the course of 15 minutes. The reaction mixture is boiled under reflux for 2 hours, the solvent is then distilled off and the residue is taken up in water. Extraction is carried out with ethyl acetate, the ethyl acetate phase is washed twice with aqueous sodium hydroxide solution and water, dried and evaporated to give 22.4 g. (89% of theory) of the title compound in the form of an oil.

(b) 1-Bromo-3-[3-(1-hydroxyhexyl)-phenoxy]-propane 19.4 g. (0.1 mole) 3-(1-hydroxyhexyl)-phenol and 80.4 g. (0.4 mole) dibromopropane are dissolved in 150 ml. methyl ethyl ketone and heated to 80° C. 15.2 g. Potassium carbonate are added thereto in the course of 1 hour. The reaction mixture is then stirred for 8 hours at 80° C., the residue is filtered off and the solvent is evaporated, together with excess dibromopropane. The residue is taken up in ethyl acetate, extracted twice with aqueous sodium hydroxide solution, washed neutral, dried and evaporated. There are obtained 25.8 g. (82% of theory) of the title compound in the form of an oil.

(c) The following compounds are obtained in a manner analogous to that described under (b)

| designation | yield % | m p. (°C.) (solvent) |
|---|---|---|
| 1-bromo-4-[3-(1-hydroxyhexyl)-phenoxy]-butane | 89 | oil |
| 1-chloro-4-[3-(1-hydroxyhexyl)-phenoxy]-but-2-ene | 85 | oil |

(d) Ethyl S-[3-(3-{1-hydroxyhexyl}-phenoxy)-2-hydroxypropyl]-4-mercaptobutyrate 9.42 g. (0.03 mole) ethyl S-(benzoisothiazol-3-yl-1,1-dioxide)-4-mercaptobutyrate are dissolved in 60 ml. acetonitrile. 2.5 ml. piperidine are added thereto under an atmosphere of nitrogen and the reaction mixture is stirred for 20 minutes at ambient temperature. Subsequently, a solution of 5.52 g. DBU and 7.5 g. (0.03 mole) [3-(1-hydroxyhexyl)-phenoxymethyl]-oxirane in 50 ml. acetonitrile is added dropwise thereto. After 1 hour at ambient temperature, the acetonitrile is distilled off and the residue is taken up in ethyl acetate, shaken out with 2M aqueous sodium hydroxide solution, washed neutral with water, dried and evaporated. The residue is stirred with diethyl ether, filtered off from insoluble material and evaporated. There are obtained 10.0 g. (84% of theory) of the title compound in the form of an oil.

(e) The following compound is obtained in manner analogous to that described under (d):

| designation | yield % | m.p. (°C.) (solvent) |
|---|---|---|
| ethyl-S—[3-(3-{1-hydroxyhexyl}-phenoxy)-propyl]-4-mercapto-butyrate | 90 | oil |

(f) S-[3-(3-{1-Hydroxyhexyl}-phenoxy)-2-hydroxypropyl]-4-mercaptobutyric acid 10.0 g. Ethyl S-[3-(3-{1-hydroxyhexyl}-phenoxy)-2-hydroxypropyl]-4-mercaptobutyrate are stirred for 2 hours at 50° C. with 50 ml. methanol and 50 ml. 2M aqueous sodium hydroxide solution. The solvent is subsequently stripped off and the residue is taken up in water and extracted three times with ethyl acetate. The aqueous phase is acidified with 2M hydrochloric acid and extracted three times with ethyl acetate. The organic phase is washed natural, dried and evaporated. There are obtained 7.4 g. (80% of theory) of the title compound in the form of an oil.

(g) The following compound is obtained in a manner analogous to that described under (f):

| designation | yield % | m.p. (°C.) (solvent) |
|---|---|---|
| S—[3-(3-{1-hydroxyhexyl}-phenoxy-)propyl]-4-mercaptobutyric acid | 85 | oil |

(h) S-[4-(3-{1-Hydroxyhexyl}-phenoxy)-but-2-enyl]-3-mercaptopropionic acid 9.15 ml. (0.105 mole) 3-mercaptopropionic acid are dissolved in 70 ml. methanol and stirred with 315 ml. 1M sodium methylate solution for 10 minutes at ambient temperature under an atmosphere of nitrogen. Subsequently, 19.79 g. (0.07 mole) 1-chloro-4-[3-(1-hydroxyhexyl)-phenoxy]-but-1-ene in 70 ml. methanol are added dropwise thereto in the course of 15 minutes. The reaction mixture is further stirred for 3 hours at ambient temperature and the solvent is then stripped off. The residue is taken up in diethyl ether and extracted several times with 2M aqueous sodium hydroxide solution. The aqueous solution is acidified with 2M hydrochloric acid and the desired compound is extracted with methylene chloride. After drying and stripping off the solvent, there are obtained 22.5 g. (91% of theory) of the title compound in the form of an oil.

(i) The following compound is obtained in a manner analogous to that described under (h)

| designation | yield % | m.p. (°C.) (solvent) |
|---|---|---|
| S—[4-(3-{1-hydroxyhexyl}-phenoxy)-butyl]-3-mercaptopropionic acid | 90 | oil |

TEST RESULTS FOR PHARMACEUTICAL ACTIVITY

Activity of the inventive compounds was shown by the following testing in vitro. The testing shows inhibition of antigen-caused constriction of passively sensitized guinea pig pulmonary parenchyma strips in vitro (Organ Bath). For this study of the inventive compounds, a measurement was made of the inhibition of the antigen-caused constriction of passively sensitized strips of guinea pig lung parenchyma, as described herewith:

Pirbright-White guinea pigs were stunned by a blow to the neck and bled. The lungs were flushed largely free of blood in situ with Krebs' buffer, pH 7.4.

Then the lung was removed, cut into strips (approx. 20×4×4 mm) and the strips were passively sensitized for one hour at room temperature with a 1:50 dilution of a homologous anti-ovalbumin antiserum and then washed once with Krebs' buffer.

The antiserum had previously been produced as described by Davies et al, (Quantitative studies on anaphylaxis in guinea pigs passively sensitized with homologous antibody. Inter. Arch. Allergy 41, 648–654 (1971)) in guinea pigs of the same strain by the repeated injection of ovalbumin (2×crystallized) with the addition of complete Freund's adjuvant.

Until it was used, the antiserum was stored undiluted at −18° C.

Then the lung strips were suspended singly in 10-milliliter water baths with a bias weight of 1.2 g on an isometric measuring receptable.

Then the baths were filled with Krebs' buffer and continually gassed at 37°° C. with $O_2$ (95%) and $CO_2$ (5%).

The constrictions of the lung strips were recorded through an amplifier on a plotter.

After a 30-minute habituating phase, histamine control spasms were produced in order to establish the reactivity of the lung specimens, washed, then the test substance was preincubated for 20 minutes at 37° C., and then the ovalbumin constriction was produced.

The inhibiting action of the compounds according to the invention was expressed as a percentage reduction of the constriction amplitude of the "specimens with the test substance" in proportion to the "untreated control constrictions."

TABLE:

| Substance from Example No. | Inhibition (%) | | | |
|---|---|---|---|---|
| | Superfusion | | Organ Bath | |
| | Concentration 20 µM | No. of Tests | Concentration 5 µg/ml | No. of Tests |
| 1 | 39 | 4 | | |
| 2b | 58 | 3 | | |
| 2c | 72 | 3 | | |
| 2f | 48 | 3 | | |
| 2g | | | 67 | 4 |
| 2i | 63 | 2 | 36 | 2 |
| 2l | 44 | 3 | | |
| 2m | 29 | 3 | | |
| 2n | 33 | 4 | | |
| 2o | 42 | 4 | | |
| 2t | 15 | 4 | | |
| 4c | 29 | 3 | | |
| 4d | 83 | 3 | | |
| 4e | 73 | 3 | | |
| 4f | 26 | 3 | | |
| 4g | 75 | 2 | | |
| 6a | 70 | 3 | | |
| 6b | 55 | 3 | | |
| 6c | 13 | 6 | | |
| 6d | | | 24 | 2 |
| 7 | 29 | 6 | | |
| 9a | 11 | 3 | | |
| 9b | 21 | 3 | | |
| 9c | 27 | 3 | | |

It will be understood that the specification and examples are illustrative but not limitative of the present invention and that other embodiments within the spirit and scope of the invention will suggest themselves to those skilled in the art.

What is claimed is:

1. A compound of the formula:

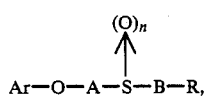

(I)

wherein
Ar is phenyl, phenyl substituted by $C_1$–$C_6$ alkyl, $C_2$–$C_6$ alkenyl, $C_1$–$C_6$ alkoxy, $C_1$–$C_6$ alkylthio, $C_1$–$C_4$ alkanoyl, hydroxyl, hydroxy-$C_1$–$C_6$-alkyl, carboxyl, $C_1$–$C_6$ alkoxy-carbonyl, carbamoyl, nitro, amino or halogen, A is a straight-chained or branched, saturated or unsaturated $C_1$–$C_8$ aliphatic hydrocarbon which is unsubstituted or substituted by a hydroxyl group, n is 0, 1 or 2, B is a straight-chained or branched, saturated or unsaturated $C_1$–$C_8$-aliphatic hydrocarbon and R is

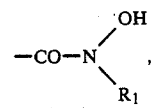

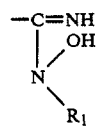

or CO—O—NH—$R_1$ wherein $R_1$ is hydrogen; $C_1$–$C_6$ alkyl; $C_1$–$C_6$-alkyl substituted by $C_3$–$C_7$ cycloalkyl; $C_2$–$C_6$-alkenyl; $C_3$–$C_7$-cycloalkyl; or ara-$C_1$–$C_6$-alkyl or aryl wherein the aromatic group contains 6–12 carbon atoms and is unsubstituted or substituted by $C_1$–$C_6$ alkyl, $C_2$–$C_6$ alkenyl, $C_1$–$C_6$-alkoxy, $C_1$–$C_6$-alkylthio, $C_1$–$C_6$-alkanoyl, hydroxyl, hydroxy-$C_1$–$C_6$-alkyl, carboxyl, $C_1$–$C_6$-alkoxy-carbonyl, carbamoyl, nitro, amino or halogen; or a pharmacologically acceptable salt thereof.

2. The compound of claim 1, wherein Ar is phenyl, phenyl substituted one or more times by propyl, pentyl, allyl, methoxy, ethoxy, acetyl, hydroxyl, 1-hydroxyhexyl or halogen, A is methylene, ethylene, propylene, butylene, pentylene, but-2-enylene, but-2-ynylene or 2-hydroxypropylene, n is 0, is methylene, ethylene, propylene, butylene or pentylene, R is

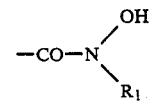

or

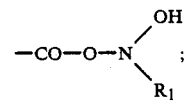

wherein $R_1$ is hydrogen, methyl, ethyl, propyl, cyclohexyl or phenyl; or a pharmacologically acceptable salt thereof.

3. The compound of claim 1, wherein Ar is phenyl substituted by propyl, allyl, hydroxyl, acetyl, chloro or 1-hydroxyhexyl, A is propylene, butylene, but-2-enylene or 2-hydroxy-propylene, n is 0, B is methylene, ethylene, propylene or pentylene and R is an N-hydroxy-N-methylamino-carbonyl or N-hydroxyaminocarbonyl; or a pharmacologically acceptable salt thereof.

4. The compound of claim 1 wherein Ar is 4-acetyl-3-hydroxy-2-propylphenyl, 3-(1-hydroxyhexyl)phenyl or 3,4-dichlorophenyl; A is but-2-ynylene, propylene, or butylene or hydroxy substituted propylene, B is ethylene, propylene, or pentylene and R is N-hydroxy-N-methylaminocarbonyl, or a pharmaceutically acceptable salt thereof.

5. The compound of claim 1 wherein R is N-hydroxy-N-methylaminocarbonyl or N-hydroxyamino carbonyl.

6. The compound of claim 1 wherein A is propylene, butylene, but-2-enylene, but-2-ynylene, or 2-hydroxypropylene.

7. The compound of claim 1 wherein B is ethylene, propylene or pentylene.

8. The compound of claim 1 designated N-hydroxy-N-methyl-S-[4-(4-acetyl-3-hydroxy-2-propylphenoxy)-butyl]-3-thiopropionic acid amide.

9. The compound of claim 1 designated N-hydroxy-N-methyl-S-[4-(acetyl-3-hydroxy-2-propylphenoxy)-but-2-ynyl]-3-thiopropionic acid amide.

10. A pharmaceutical composition for combating allergic diseases containing an effective amount to combat allergic diseases of the compound of claim 1 in a pharmaceutically acceptable carrier.

11. The pharmaceutical composition of claim 10 wherein said compound is .

12. A method for combating allergic diseases in a patient suffering from an allergic disease comprising administering an effective amount to combat said allergic disease, of the compound of claim 1 or a pharmaceutically acceptable salt thereof.

13. The method of claim 12 wherein 0.1 to 50 mg/kg body weight is administered daily.

14. A method for combating allergic diseases in a patient suffering from an allergic disease comprising administering an effective amount to combat said allergic disease, of the pharmaceutical composition of claim 10.

15. A method for combating allergic diseases in a patient suffering from an allergic disease comprising administring an effective amount to combat said allergic disease of the pharmaceutical composition of claim 11.

* * * * *

UNITED STATES PATENT AND TRADEMARK OFFICE
CERTIFICATE OF CORRECTION

PATENT NO. : 4,906,666
DATED : March 6, 1990
INVENTOR(S) : Erhard Reinholz, et al.

It is certified that error appears in the above-identified patent and that said Letters Patent is hereby corrected as shown below:

Col. 9, line 28: delete "S-[3-4-Acetyl" and insert -- S-[3-(4-Acetyl --.

Col. 12, line 65: delete "37°°C" and insert -- 37°C --.

Col. 14, line 33: after "n is 0," insert -- B --.
(Claim 2, line 6)

Col. 15, line 17: after "compound is" insert -- N-hydroxy-N-methyl-
(Claim 11, line 2) S-[4-(4-acetyl-3-hydroxy-2-propylphenoxy)-
butyl]-3-thiopropionic acid amide and
N-hydroxy-N-methyl-S-[4-(acetyl-3-hydroxy-2-
propylphenoxy)-but-2-ynyl]-3-thiopropionic
acid amide. --

Signed and Sealed this

Nineteenth Day of November, 1991

Attest:

HARRY F. MANBECK, JR.

*Attesting Officer*  *Commissioner of Patents and Trademarks*